United States Patent [19]

Bochis et al.

[11] Patent Number: 4,622,330

[45] Date of Patent: Nov. 11, 1986

[54] ANTIPROTOZOAL 3-AMINO OR SUBSTITUTED AMINO PYRAZOLES

[75] Inventors: Richard J. Bochis, E. Brunswick; Richard A. Dybas, Bridgewater; Edward F. Rogers, Middletown, all of N.J.

[73] Assignee: Merck & Co., Inc., Rahway, N.J.

[21] Appl. No.: 622,337

[22] Filed: Jun. 19, 1984

Related U.S. Application Data

[63] Continuation-in-part of Ser. No. 450,847, Dec. 20, 1982, abandoned.

[51] Int. Cl.$^4$ .................... A01N 43/56; A01N 43/78; C07D 231/52; C07D 417/04
[52] U.S. Cl. .................... 514/313; 514/314; 514/341; 514/370; 514/372; 514/404; 514/407; 546/162; 546/167; 546/172; 546/174; 546/175; 546/176; 546/279; 548/193; 548/194; 548/197; 548/198; 548/214; 548/362; 548/365; 548/375; 548/376; 548/377
[58] Field of Search ............ 546/162, 167, 172, 174, 546/175, 176, 279; 548/362, 365, 375, 376, 377, 193, 194, 197, 198, 214; 514/404, 406, 407, 313, 314, 341, 370, 372

[56] References Cited

U.S. PATENT DOCUMENTS 3,864,359  2/1975  Marsico, Jr. et al. ............ 548/362

FOREIGN PATENT DOCUMENTS 10508  3/1974  Japan ................................ 548/362

OTHER PUBLICATIONS

Schmidt et al., Chem. Abst. 53, 20069i, (1959).
Sutcliffe et al., Chem. Abst. 57, 11197d, (1962).
Kreutzberger et al., Chem. Abst., 92, 128862z, (1980).
Kreutzberger et al., Chem. Abst., 94, 139746g (1981).
Chemical Abstracts, vol. 66, (1966) pp. 28I to 40I.
Derwent Abstract 26117v/14, (1974).

Primary Examiner—Richard A. Schwartz
Assistant Examiner—Kurt G. Briscoe
Attorney, Agent, or Firm—David L. Rose; Michael C. Sudol, Jr.

[57] ABSTRACT

Novel 3-amino or substituted amino pyrazoles are disclosed as having antiprotozoal and antiparasitic activity in particular anticoccidial activity and are useful for controlling cecal and or intestinal coccidiosis when administered in minor quantities to animals, in particular to poultry usually in admixture with animal sustenance.

7 Claims, No Drawings

ANTIPROTOZOAL 3-AMINO OR SUBSTITUTED AMINO PYRAZOLES

CROSS REFERENCE TO RELATED APPLICATIONS

This application is a continuation-in-part of our application Ser. No. 450,847 filed Dec. 20, 1982, which is now abandoned.

BACKGROUND OF THE INVENTION

This invention relates to new chemical compounds and the method of the preparation of the same. It relates further to the use of such new compounds for treating and preventing protozoal parasitic diseases. This invention still more particularly relates to novel 3-amino and substituted amino pyrazole compounds and substituted derivatives thereof and the use of the same in the control and treatment of protozoal diseases, particularly coccidiosis.

Coccidiosis is a wide-spread poultry disease which is produced by infections of protozoa of the genus Eimeria which causes severe pathology in the intestines and ceca of poultry. Some of the most significant of these species are E. tenella, E. acervulina, E. necatrix, E. brunetti and E. maxima. This disease is generally spread by the birds picking up the infectious organism in droppings on contaminated litter or ground or by way of food or drinking water. The disease is manifested by hemorrhage, accumulation of blood in the ceca, passage of blood to the droppings, weakness and digestive disturbances. The disease often terminates in the death of the animal but the fowl which survive severe infections have had their market value substantially reduced as a result of the infection. Coccidiosis is therefore a disease of great economic importance and extensive work has been done to find new and improved methods for controlling and treating coccidial infections in poultry.

SUMMARY OF THE INVENTION

This invention is based on the discovery that certain novel 3-amino and substituted amino pyrazoles as well as substituted derivatives thereof have a surprisingly and unexpectedly high degree of activity against coccidiosis of poultry. Administration of a small amount of at least one of these compounds preferably by combination with poultry feed is effective in preventing or greatly reducing the incidence of coccidiosis. The compounds are effective against both the cecal form (caused by E. tenella) and the intestinal forms (principally caused by E. acervulina, E. brunetti, E. maxima and E. necatrix). The coccidiostats of this invention are particularly effective against the species that cause cecal damage in addition to preventing the pathology caused by the coccidia. These compounds also exert an inhibitory effect on the oocysts by greatly reducing the number and or the sporulation of those produced.

The instant compounds are also active against other protozoal diseases such as other Eimeria spp in other animals, Trypanosoma cruzi, Leishmania spp, Plasmodium spp, Babesia spp, Trichomonadidae spp, Histomonas spp, Giardia spp, Toxoplasma spp, Entamoeba histolytica, Theileria spp, and the like.

The novel pyrazole derivatives of this invention are prepared by reacting a substituted hydrazine compound with a substituted malononitrile to prepare the 4-cyano compound. Other 4-substituents can be prepared from the 4-cyano.

It is therefore a primary object of this invention to provide novel 3-amino or substituted amino pyrazoles with appropriate substitutions at the 2, 3, 4 and 5 positions which are useful in the control of protozoal diseases. Another object of this invention is to provide novel antiprotozoal and in particular anticoccidial agents. Still another object of this invention is to provide novel feed compositions useful for the prevention and supression of protozoal diseases. A further object of this invention is to provide a new and useful method for the control of coccidiosis in poultry which comprises administering to the poultry minor amounts of the anticoccidial substance of this invention. A still further object of this invention is to provide a method and alternate methods for preparing novel 3-amino and substituted amino pyrazoles. These and further objects of this invention will become apparent from reading the following description.

DESCRIPTION OF THE INVENTION

The novel compounds of this invention are best realized in the following structural formula:

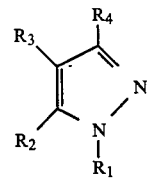

wherein:

$R_1$ is phenylalkyl, or substituted phenyl alkyl wherein the substituents are one or more of halogen, cyano, trifluoromethyl, loweralkanoyl, nitro, loweralkyl, loweralkoxy, carboxy, carbalkoxy, acetamido, benzoyl, halobenzoyl, trifluoromethylbenzoyl, phenoxy, halophenoxy, trifluormethylphenoxy, phenyl, halophenyl, trifluoromethylphenyl, phenylthio, phenylsulfinyl, phenylsulfonyl, halo or trifluoromethyl substituted phenylthio, halo or trifluoromethyl substituted phenylsulfinyl, halo or trifluoromethyl substituted phenylsulfonyl, loweralkylthio, loweralkylsulfinyl, or loweralkysulfonyl, provided that $R_1$ is unsubstituted phenylalkyl only when $R_3$ is other than cyano;

$R_1$ may also be phenacyl, 3-phenyl-2-propenyl, phenoxyethyl, pyridyl, pyridylmethyl, thiazolyl, naphthyl, naphthylmethyl, quinolyl or quinolylmethyl;

$R_2$ is amino, mono or diloweralkyl amino acetamido, acetamido, ureido, formamido, formimino or guanidino;

$R_3$ is carbamoyl, cyano, carbazoyl, amidino or N-hydroxycarbamoyl; and $R_4$ is hydrogen, loweralkyl, hydroxy, amino, mono or disubstituted loweralkyl amino, phenyl, cyano, loweralkoxy, loweralkanoyloxy, loweralkylthio, loweralkylsulfinyl or loweralkylsulfonyl. Provided that when $R_3$ is cyano, the substituent on the $R_1$ group is other than meta trifluoromethyl, and when $R_3$ is carbamoyl, $R_1$ is other than pyridyl.

The preferred compounds of the instant invention are realized in the foregoing structural formula wherein:

$R_1$ is benzyl or substituted benzyl wherein the substituents are 1 to 3 of halo, cyano, trifluoromethyl, phenoxy, phenylthio, phenylsulfinyl, phenylsulfonyl, benzoyl, halo or trifluoromethyl substituted phenoxy, halo or trifluoromethyl substituted phenylthio, halo or trifluoromethyl substituted phenylsulfinyl, halo or trifluoromethyl substituted phenyl sulfonyl; or halo or trifluoromethyl substituted benzoyl;

$R_2$ is amino or mono or diloweralkyl amino;
$R_3$ is carbamoyl or cyano; and
$R_4$ is hydrogen or loweralkyl.

The most preferred compounds of the instant invention are realized in the foregoing structural formula wherein $R_1$ is substituted benzyl wherein the substituents are 2 or 3 of halo, cyano, trifluoromethyl, halo or trifluoromethylphenoxy, halo or trifluoromethyl phenylthio, halo or trifluoromethylphenylsulfinyl or halo or trifluoromethyl sulfonyl or halo or trifluoromethyl benzoyl;

$R_2$ is amino;
$R_3$ is carbamoyl or cyano; and
$R_4$ is hydrogen.

In the instant invention the term "loweralkyl" is intended to include those alkyl groups containing from 1- to 3-carbon atoms. Exemplary of such groups are methyl, ethyl, propyl and isopropyl.

The term "loweralkoxy" is intended to include those alkoxy groups containing from 1 to 3 carbon atoms in either a straight or branched configuration. Exemplary of such groups are methoxy, ethoxy, propoxy, and isopropoxy.

The term "loweralkanoyl" is intended to include those alkanoyl groups containing 2 or 3 carbon atoms exemplified by acetyl and propionyl.

The compounds of the instant invention may be prepared by any one of several processes. The most general process is outlined in the following reaction scheme.

The following reaction scheme is used to prepare pyrazole compounds wherein $R_2$ is amino and $R_3$ is cyano or carbamoyl.

Reaction Scheme

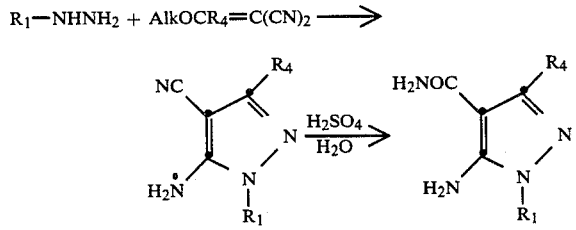

In the first step of the foregoing reaction scheme the compounds wherein $R_3$ is cyano are prepared and the reaction is carried out in a loweralkanol, preferably ethanol, by stirring the $R_1$ substituted hydrazine compound with a substituted malononitrile at from room temperature to 100° C. or the reflux temperature of the reaction mixture for from 15 minutes to 10 hours. On occasion, the hydrazine compound is obtained as an acid addition salt thereof and before such a compound can be reacted the free base must be liberated. In such cases the free base may be prepared separately or a base such as an alkali metal alkoxide can be added to the reaction mixture. The product wherein $R_3$ is cyano is isolated from the reaction mixture using techniques known to those skilled in the art and if desired can be hydrolyzed to the carbamoyl compound as shown in the second step of the foregoing reaction scheme by combining with an excess of concentrated sulfuric acid at from 0° to 10° C. followed by hydrolysis with water. The cyano compound is added to the cold concentrated sulfuric acid in portions over a period of up to 3 hours, generally, however, from ½ to 1 hour, followed by hydrolysis by pouring the acid mixture onto an excess of ice-water or ice chips. The product precipitate and is isolated by techniques known to those skilled in the art.

The novel compounds of this invention are orally administered to poultry for the control and prevention of coccidiosis. Any number of conventional methods are suitable for administering the coccidiostats of this invention to poultry, as for example, they may be given in the poultry feed. The actual quantity of the coccidiostats administered to the poultry in accordance with this invention will vary over a wide range and be adjusted to individual needs, depending upon the species of the coccidia involved and severity of the infection. The limiting criteria are that the minimum amount is sufficient to control coccidiosis and the maximum amount is such that the coccidiostat does not result in any undesirable effects.

A feed typically contains from about 0.003 to about 0.2 percent, preferably from about 0.005 to about 0.1 percent, by weight of one of the coccidiostats of this invention. The optimum levels will naturally vary with the specific compound utilized and species of Eimeria involved, and can be readily determined by one skilled in the art. Levels of the 3-amino and substituted amino pyrazoles of this invention, in poultry feed of from about 0.001 percent to about 0.1 percent by weight of the diet are especially useful in controlling the pathology associated with *E. tenella*, as well as the intestinal dwelling species.

Depending on the compound employed, levels of 0.003 percent to 0.006 percent possess the novel effects of reducing the number of oocysts passed in the droppings of infected chickens and/or inhibiting the subsequent division and maturation to infectivity, scientifically designated as the process of sporulation. Thus, the combination of prevention of pathology, coupled with the inhibiting effect on the reproductive product of these organisms, the oocysts, present a unique two-fold method for the control of coccidiosis in poultry.

The quantity or concentration of a novel coccidiostat of this invention in any admixture in which it is administered to the poultry will, of course, vary in accordance with the type of admixture utilized.

Of the various methods of administering the coccidiostats of this invention to poultry, they are most conveniently administered as a component of a feed composition. The novel coccidiostats may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal and calcium carbonate and vitamins.

The following non-limiting examples will serve to further illustrate the instant invention.

EXAMPLE 1

Preparation of 3-amino-4-cyano-2-substituted pyrazoles

A solution of substituted hydrazine (or substituted hydrazine hydrochloride and 1 mole equivalent sodium methoxide) in ethanol at 80° was treated with ethoxymethylenemalononitrile (1 mole equivalent) in portions. The mixture was refluxed for 2-5 hours, cooled, filtered, washed, and recrystallized to provide the 3-amino-4-cyano-2-substituted pyrazole.
| $R_1$—NHNH$_2$ | NaOCH$_3$ wt. (g) | EtOCH=C(CN)$_2$ wt. (g) | EtOH (ml) | time of reflux (hour) | washing solvent | recrystallization solvent | Product 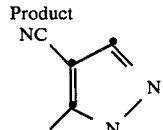 | yield (g) | m.p. (°C.) |
|---|---|---|---|---|---|---|---|---|---|
| 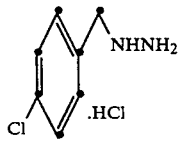 | 3.50 | 0.98 | 2.20 | 50 | 4 | H$_2$O | EtOH—H$_2$O | 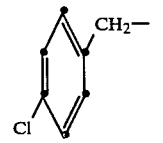 | 2.90 | 165–168 |
| 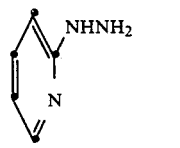 | 10.9 | — | 12.2 | 100 | 4 | — | EtOH | 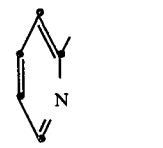 | 14.9 | 190.5–191.5 |
| 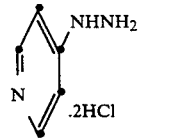 | 9.10 | 5.40 | 6.10 | 75 | 5 | — | — | 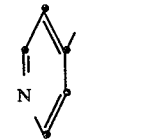 | 8.40 | |
| 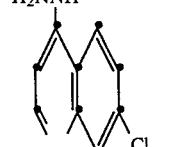 | 9.68 | — | 6.10 | 150 | 2 | Et$_2$O | — | 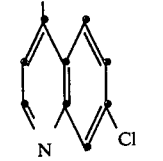 | 10.0 | |
| 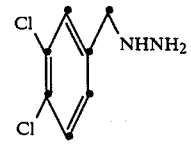 | 14.8 | — | 10.12 | 50 | 0.75 | EtOH | EtOH | 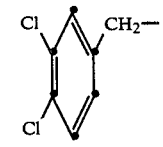 | 13.52 | 169–172 |
| 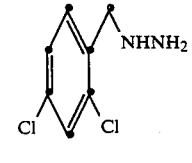 | 14.8 | — | 10.12 | 50 | 0.75 | EtOH | — | 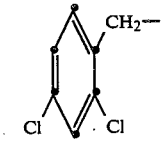 | 13.98 | |
| 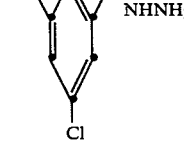 | 12.45 | — | 8.52 | 42 | 1 | ** | — | 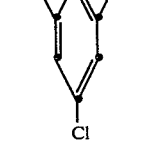 | 11.1 | 142.5–145 |
| 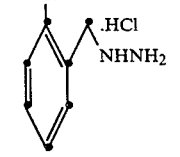 | 4. | 1.08 | 2.6 | 15 | 0.5 | *** | — | 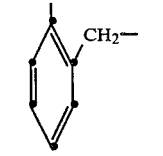 | 4.65 | 133–135° |

-continued

| $R_1-NHNH_2$ | wt. (g) | NaOCH$_3$ wt. (g) | EtOCH=C(CN)$_2$ wt. (g) | EtOH (ml) | time of reflux (hour) | washing solvent | recrystal- lization solvent | Product 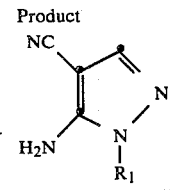 | yield (g) | m.p. (°C.) |
|---|---|---|---|---|---|---|---|---|---|---|
| 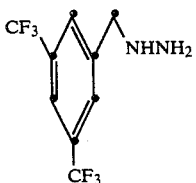 | 6.4 | — | 3.24 | 16 | 0.5 | **** | — | 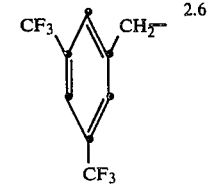 | 2.6 | |

** Isolated by chromatography on 375 g silica gel, 9:1 (v/v) CH$_2$Cl$_2$/Et$_2$O eluent.
*** Isolated by chromatography on 200 g silica gel, CH$_2$Cl$_2$ eluent.
**** Isolated by chromatography on 200 g silica gel, 9:1 (v/v) CH$_2$Cl$_2$/Et$_2$O eluent.

EXAMPLE 2

Preparation of 3-amino-2-substituted pyrazole-4-carboxamides

Solid 3-amino-4-cyano-2-substituted pyrazole was added in small portions to concentrated sulfuric acid at 0°–10° C. The mixture was stirred until homogeneous, poured onto ice, and made basic with concentrated ammonium hydroxide. The precipitate was collected, washed with water, and recrystallized.

| $R_1 =$ | 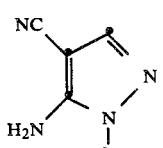 wt. (g) | H$_2$SO$_4$ (ml) | 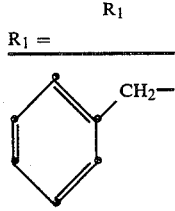 (g) | recrystal- lization solvent | melting point (°C.) |
|---|---|---|---|---|---|
| 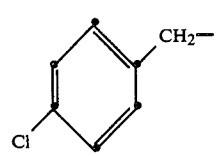 | 7.5 | 30 | 3.7 | EtOH | 223–225 |
| 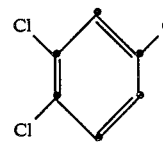 | 3.10 | 15 | 1.54 | EtOH | 242–244 |
| 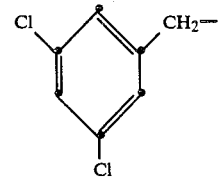 | 7.5 | 30 | 4.51 | EtOH | 226–228 |
| | 7.5 | 30 | 4.4 | EtOH | 202–203.5 |

-continued

| $R_1 =$ | wt. (g) | $H_2SO_4$ (ml) | $H_2N$ yield $R_1$ (g) | recrystal- lization solvent | melting point (°C.) |
|---|---|---|---|---|---|
| CF₃-C₆H₄-CH₂— (3-CF₃ benzyl) | 6.9 | 27 | 3.9 | EtOH | 216–217.5 |
| 2-Cl-C₆H₄-CH₂— | 2.5 | 10 | 1.88 | EtOH | 209–210° |
| 3,5-(CF₃)₂-C₆H₃-CH₂— | 2.5 | 10 | 1.36 | EtOH | 252–253 |

Other 2-substituted-3-amino-4-cyanopyrazoles

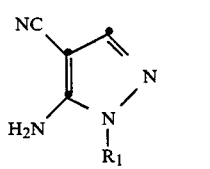

and 2-substituted-3-aminopyrazole-4-carboxamides

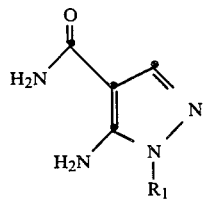

which can be prepared by the procedures of Examples 1–5:

| $R_1$ | $R_1$ | $R_1$ |
|---|---|---|
| 2-Cl-C₆H₄-CH₂— | 4-NC-C₆H₄-CH₂— | 3,4-(CF₃)₂-C₆H₃-CH₂— |
| 3-Cl-C₆H₄-CH₂— | 4-CF₃-C₆H₄-CH₂— | 3,4-Br₂-C₆H₃-CH₂— |

-continued
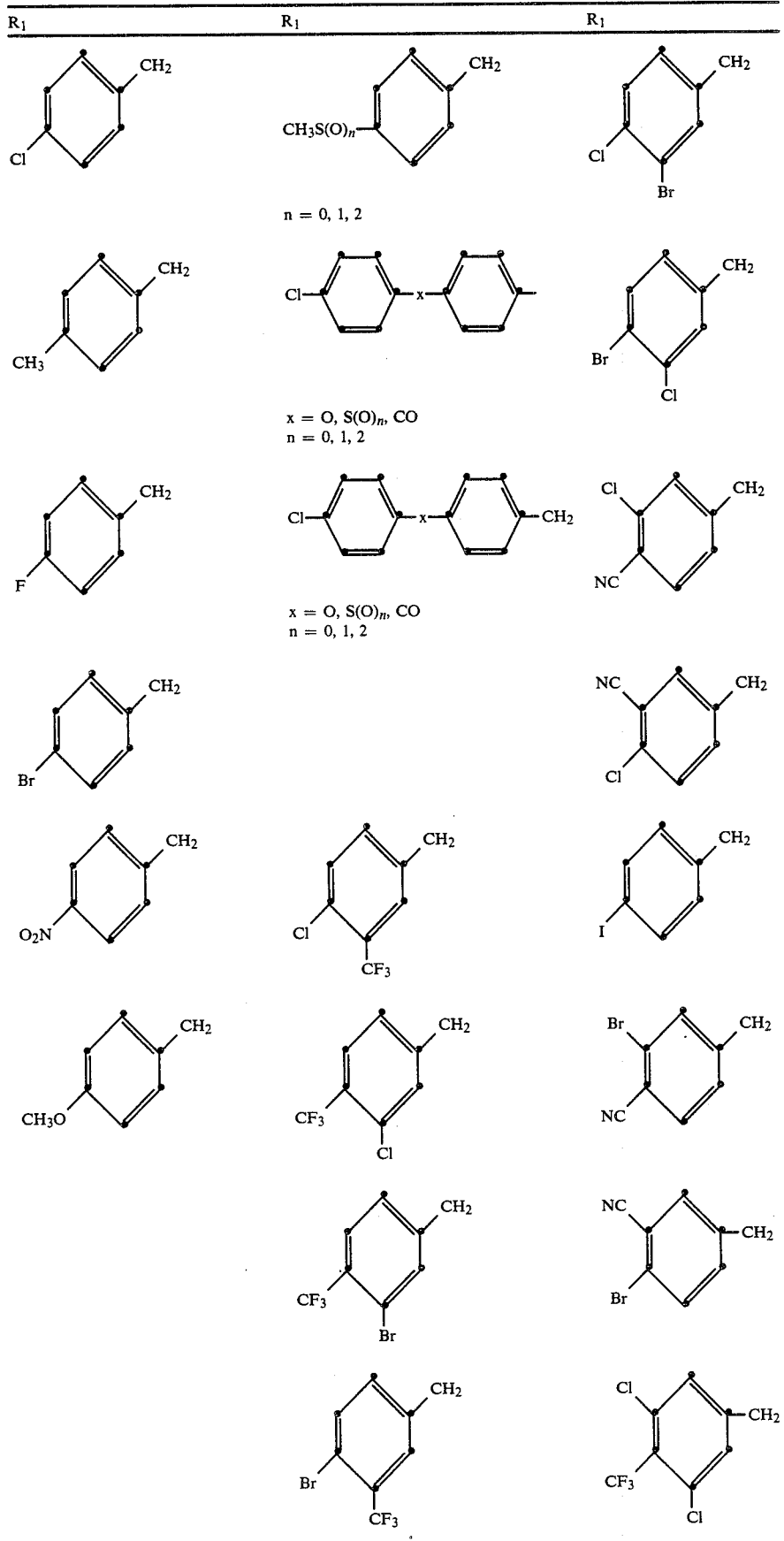

-continued

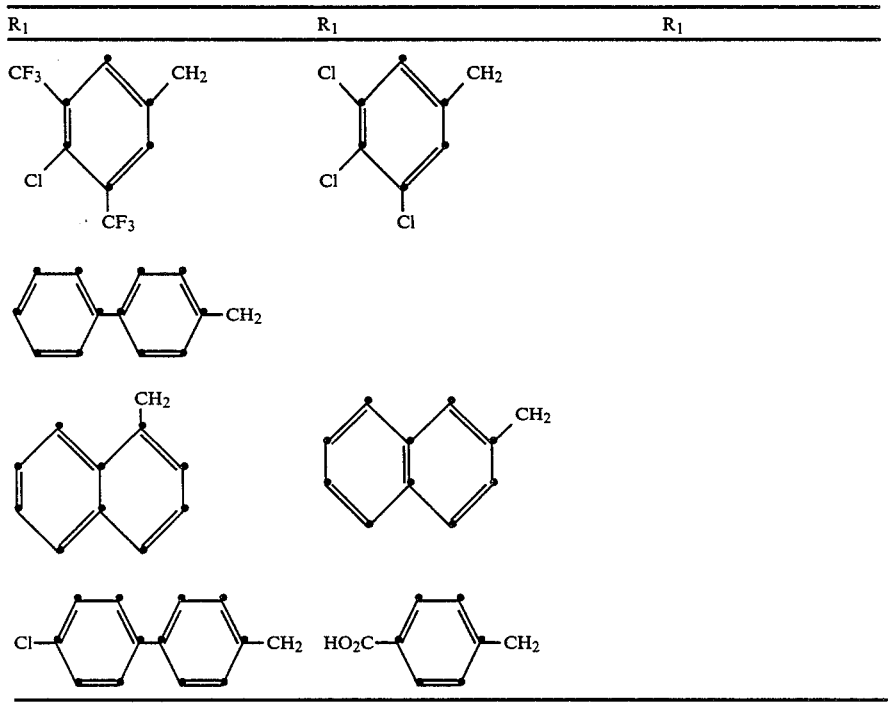

What is claimed is:

1. A compound having the formula:

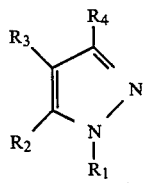

wherein:

R₁ is substituted phenyl alkyl (1–3 carbon chain) wherein the substituents are one or more of halogen, cyano, trifluoromethyl, loweralkanol, nitro, loweralkyl, loweralkoxy, carboxy, carbalkoxy (1–3 carbon chain), acetamido, benzoyl, halobenzoyl, trifluoromethylbenzoyl, phenoxy, halophenoxy, trifluoromethylphenoxy, phenyl, halophenyl, trifluoromethylphenyl, phenylthio, phenylsulfinyl, phenylsulfonyl, halo or trifluoromethyl substituted phenylthio, halo or trifluoromethyl substituted phenylsulfinyl, halo or trifluoromethyl substituted phenylsulfonyl, loweralkylthio, loweralkylsulfinyl, or loweralkylsulfonyl, provided that R₁ is unsubstituted phenylalkyl only when R₃ is other than cyano;

R₁ may also be phenacyl, 3-phenyl-2-propenyl, phenoxyethyl, pyridyl, pyridylmethyl, thiazolyl, naphthyl, naphthylmethyl, quinolyl, or quinolylmethyl;

R₂ is amino, mono or diloweralkylamino, acetamido, acetimido, ureido, formamido, formimido or guanidino;

R₃ is carbamoyl, carbazoyl, amidino or N-hydroxycarbamoyl; and

R₄ is hydrogen, loweralkyl, hydroxy, amino, mono or diloweralkylamino, phenyl, cyano, loweralkoxy, loweralkanoyloxy, loweralkylthio, loweralkylsulfinyl, or loweralkylsulfonyl; provided that when R₃ is carbamoyl, R₂ is other than pyridyl.

2. The compound of claim 1 wherein R₁ is substituted benzyl wherein the substituents are 1 to 3 of halo, cyano, trifluoromethyl, phenoxy, phenylthio, phenylsulfinyl, phenylsulfonyl, benzoyl, halo or trifluoromethyl substituted phenoxy, halo or trifluoromethyl substituted phenylthio, halo or trifluoromethyl substituted phenyl sulfinyl, halo or trifluoromethyl substituted phenyl sulfonyl, or halo or trifluoromethyl substituted benzoyl, provided that when R₁ is benzyl R₃ is other than cyano;

R₂ is amino or mono or diloweralkylamino;

R₃ is carbamoyl; and

R₄ is hydrogen or loweralkyl.

3. The compound of claim 2 wherein R₁ is substituted benzyl wherein the substituents are 2 or 3 of halo, cyano, trifluoromethyl, halo or trifluoromethylphenoxy, halo or trifluoromethyl phenylthio, halo or trifluoromethyl phenylsulfinyl, halo or trifluoromethyl phenyl sulfonyl, or halo or trifluoromethyl benzoyl;

R₂ is amino;

R₃ is carbamoyl; and

R₄ is hydrogen.

4. A composition useful for the prevention and treatment of protozoal diseases which comprises an inert carrier and an effective amount of a compound having the formula:

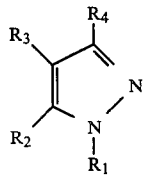

wherein:

R₁ is phenylalkyl (1-3 carbon chain) or substituted phenyl alkyl wherein the substituents are one or more of halogen, cyano, trifluoromethyl, loweralkanoyl, nitro, loweralkyl, loweralkoxy, carboxy, carbalkoxy (1-3 carbon chain), acetamido, benzoyl, halobenzoyl, trifluoromethylbenzoyl, phenoxy, halophenoxy, trifluoromethylphenoxy, phenyl, halphenyl, trifluoromethylphenyl, phenylthio, phenylsulfinyl, phenylsulfonyl, halo or trifluoromethyl substituted phenylthio, halo or trifluoromethyl substituted phenylsulfinyl, halo or trifluoromethyl substituted phenylsulfonyl, loweralkylthio, loweralkylsulfinyl, or loweralkylsulfonyl, provided that R₁ is unsubstituted phenylalkyl only when R₃ is other than cyano;

R₁ may also be phenacyl, 3-phenyl-2-propenyl, phenoxyethyl, pyridyl, pyridylmethyl, thiazolyl, naphthyl, naphthylmethyl, quinolyl, or quinolylmethyl;

R₂ is amino, mono or diloweralkylamino, acetamido, acetimido, ureido, formamido, formimido or quanidino;

R₃ is carbamoyl, cyano, carbazoyl, amidino or N-hydroxycarbamoyl; and

R₄ is hydrogen, loweralkyl, hydroxy, amino, mono or diloweralkylamino, phenyl, cyano, loweralkoxy, loweralkanoyloxy, loweralkylthio, loweralkylsulfinyl, or loweralkylsulfonyl; provided that when R₃ is carbamoyl, R₂ is other than pyridyl.

5. The composition of claim 4 wherein the protozoal disease is coccidiosis.

6. A method for preventing or treating protozoal diseases which comprises administering to an animal in need of such treatment an effective amount of a compound having the formula:

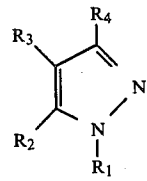

wherein:

R₁ is phenylalkyl (1-3 carbon chain) or substituted phenyl alkyl wherein the substituents are one or more of halogen, cyano, trifluoromethyl, loweralkanoyl, nitro, loweralkyl, loweralkoxy, carboxy, carbalkoxy (1-3 carbon chain), acetamido, benzoyl, halobenzoyl, trifluoromethyl-benzoyl, phenoxy, halophenoxy, trifluoromethyl-phenoxy, phenyl, halophenyl, trifluoromethylphenyl, phenylthio, phenylsulfinyl, phenylsulfonyl, halo or trifluoromethyl substituted phenylthio, halo or trifluoromethyl substituted phenylsulfinyl, halo or trifluoromethyl substituted phenylsulfonyl, loweralkylthio, loweralkylsulfinyl, or loweralkylsulfonyl, provided that R₁ is unsubstituted phenylalkyl only when R₃ is other than cyano;

R₁ may also be phenacyl, 3-phenyl-2-propenyl, phenoxyethyl, pyridyl, pyridylmethyl, thiazolyl, naphthyl, naphthylmethyl, quinolyl, or quinolylmethyl;

R₂ is amino, mono or diloweralkylamino, acetamido, acetimido, ureido, formamido, formimido or quanidino;

R₃ is carbamoyl, cyano, carbazoyl, amidino or N-hydroxycarbamoyl; and

R₄ is hydrogen, loweralkyl, hydroxy, amino, mono or diloweralkylamino, phenyl, cyano, loweralkoxy, loweralkanoyloxy, loweralkylthio, loweralkylsulfinyl, or loweralkylsulfonyl; provided that when R₃ is carbamoyl, R₂ is other than pyridyl.

7. The method of claim 6 wherein the protozoal disease is coccidiosis.

* * * * *